United States Patent
Yamada et al.

(10) Patent No.: US 8,434,478 B2
(45) Date of Patent: May 7, 2013

(54) AEROSOL INHALATOR

(75) Inventors: Manabu Yamada, Tokyo (JP);
Kazuhiko Katayama, Tokyo (JP);
Hiroshi Sasaki, Tokyo (JP)

(73) Assignee: Japan Tobacco Inc., Tokyo (JP)

( * ) Notice: Subject to any disclaimer, the term of this patent is extended or adjusted under 35 U.S.C. 154(b) by 601 days.

(21) Appl. No.: 12/794,169

(22) Filed: Jun. 4, 2010

(65) Prior Publication Data
US 2010/0242956 A1 Sep. 30, 2010

Related U.S. Application Data

(63) Continuation of application No. PCT/JP2008/071017, filed on Nov. 19, 2008.

(30) Foreign Application Priority Data

Dec. 5, 2007 (JP) ................................. 2007-314823

(51) Int. Cl.
*A61M 11/00* (2006.01)
(52) U.S. Cl.
USPC ............. 128/203.26; 128/200.14; 128/203.15
(58) Field of Classification Search ............. 128/203.26, 128/200.14, 200.23, 200.19, 200.22, 203.12, 128/203.15, 203.21, 203.16, 203.17; 219/5, 219/530, 538; 261/DIG. 65
See application file for complete search history.

(56) References Cited

U.S. PATENT DOCUMENTS

| | | | |
|---|---|---|---|
| 4,942,874 A * | 7/1990 | Terada et al. ............. | 128/203.16 |
| 4,947,874 A | 8/1990 | Brooks et al. | |
| 5,186,164 A * | 2/1993 | Raghuprasad ........... | 128/200.14 |
| 5,743,251 A | 4/1998 | Howell et al. | |
| 6,694,975 B2 * | 2/2004 | Schuster et al. ......... | 128/203.26 |
| 6,845,771 B1 * | 1/2005 | Love ........................ | 128/203.12 |
| 2002/0078948 A1 | 6/2002 | Hindle et al. | |

FOREIGN PATENT DOCUMENTS

| | | |
|---|---|---|
| EP | 0 358 002 A2 | 3/1990 |
| JP | 2-124082 A | 5/1990 |
| JP | 8-189573 A | 7/1996 |
| JP | 11-89551 A | 4/1999 |
| JP | 2000-510763 A | 8/2000 |
| JP | 2003-530980 A | 10/2003 |
| JP | 2005-525131 A | 8/2005 |
| SU | 1750694 A1 | 7/1992 |
| WO | WO 97/42993 A2 | 11/1997 |
| WO | WO 01/81182 A2 | 11/2001 |
| WO | WO 03/012565 A1 | 2/2003 |

* cited by examiner

*Primary Examiner* — Steven Douglas
(74) *Attorney, Agent, or Firm* — Birch, Stewart, Kolasch & Birch, LLP

(57) ABSTRACT

An aerosol inhalator has an aerosol generation passage extending from an ambient air inlet (2) to a mouthpiece (4), a liquid supply device (18) for feeding a predetermined amount of a solution to a feed position (A) in the passage (6), a ceramic heater (12) for heating the solution conveyed from the feed position (A) toward the mouthpiece (4) with a drawn-in flow of air created in the passage (6) by a user's sucking action, thereby causing the solution to evaporate and turn into an aerosol in the passage (6), and a protector provided at least either at a location near the feed position (A) or at a location between the feed position (A) and the liquid supply device (18), the protector having at least one of a radiation cover (2), a cooling device (21) and an open-close valve (22).

10 Claims, 3 Drawing Sheets

LOW-TEMPERATURE ENVIRONMENT

HIGH-TEMPERATURE ENVIRONMENT

AEROSOL INHALATOR

CROSS REFERENCE TO RELATED APPLICATIONS

This application is a Continuation of PCT International Application No. PCT/JP2008/071017 filed on Nov. 19, 2008, which claims the benefit of Patent Application No. 2007-314823 filed in Japan on Dec. 5, 2007. The entire content of all of the above applications is hereby incorporated by reference into the present application.

TECHNICAL FIELD

This invention relates to an aerosol inhalator for delivering medicaments, refreshing/relaxing materials or the like to a user in aerosol form.

BACKGROUND ART

An aerosol inhalator of this type is disclosed in Japanese Patent KOHYO Publication 2000-510763, for example. The inhalator in this publication includes a supply pump for supplying a solution (liquid material) from which an aerosol is generated. The supply pump is connected to a tube. The tube has an open end and becomes filled with the solution supplied by the supply pump. A mouthpiece is provided adjacent to the open end of the tube, and an electric heater is provided to surround the end portion of the tube. The electric heater heats the solution in the end portion of the tube, thereby causing it to evaporate, and the resulting vapor of the solution spurts out of the open end of the tube by itself. The vapor of the solution condenses by coming in contact with the air drawn in through the mouthpiece by the user, and turns into an aerosol, which the user can inhale with drawn-in air.

DISCLOSURE OF THE INVENTION

Problem to be Solved by the Invention

In the use of the inhalator disclosed in the above publication, the tube is open to ambient air via the mouthpiece. In addition, the end portion of the tube is always exposed to heat from the electric heater. Consequently, if the solution contains volatile constituents, heat from the electric heater causes the volatile constituents to evaporate and escape from the solution in the tube, and causes thermal degradation of the solution. For this reason, the solution, and therefore, the aerosol cannot maintain stable quality.

An object of the present invention is to provide an aerosol inhalator allowing sucking of an aerosol with stable quality.

Means for Solving the Problem

The above object is achieved by an aerosol inhalator according to the present invention, which comprises an aerosol generation passage extending from an ambient air inlet to a mouthpiece; a liquid supply device including a liquid chamber storing a solution from which an aerosol is to be generated, for being capable of feeding a predetermined amount of the solution to a feed position defined in the aerosol generation passage; a heating device disposed on the aerosol generation passage, downstream of the feed position, for heating the solution conveyed from the feed position toward the mouthpiece with a drawn-in flow of air created in the aerosol generation flow passage by the mouthpiece being sucking on, thereby causing the solution to evaporate and turn into an aerosol; and a protector provided on a pathway from the heating device to the liquid supply device via the feed position, to protect the solution at the feed position and in the liquid chamber from environment.

Specifically, the protector may include a reduction device arranged near the feed position to reduce heat transfer from the heating device to the feed position. The reduction device may include a radiation member surrounding the aerosol generation passage.

In the above-described aerosol inhalator, the heating device heats the solution which is being conveyed from the feed position toward the mouthpiece by a sucking action, thereby causing the solution to evaporate and turn into an aerosol.

Even if the heating device is kept operating to keep the aerosol inhalator ready for use, heat transferred from the heating device to the feed position is dissipated by the reduction device, specifically the radiation member, so that the temperature around the feed position is kept at the level that can prevent the solution from evaporating and escaping.

The protector may include a cooling device in place of or in addition to the reduction device.

The protector may include a valve arranged between the feed position and the liquid supply device, in place of or in addition to the reduction device and/or the cooling device. It may be arranged such that the valve is held open only while air in the aerosol generation passage is being sucked through the mouthpiece.

The valve can therefore seal the liquid chamber of the supply device, between the feed position and the liquid supply device, thereby protecting the solution in the liquid chamber from the environment.

Specifically, the valve may include an elastically-deformable tube connecting the feed position and the liquid supply device, the tube having a part as a valve passage, and a movable member disposed near the tube to be movable between a "close" position in which the movable member elastically deforms and squeezes the tube to close the valve passage and an "open" position in which the movable member is drawn back from the tube to open the valve passage.

The valve may further include a fixed member capable of pinching the tube in cooperation with the movable member, a valve spring holding the movable member in the "close" position, and an actuator for moving the movable member to the "open" position against urging force of the valve spring.

Specifically, the actuator may include a magnet mounted on the movable member and a solenoid capable of attracting the magnet, or includes a control spring made of a shape-memory alloy.

Effect of the Invention

The protector of the aerosol inhalator protects the solution at the feed position and in the liquid chamber of the liquid supply device from the environment, thus preventing the solution from evaporating and escaping, and undergoing alteration. This allows all the amount of the solution fed to the feed position by the liquid supply device to turn into an aerosol and be inhaled by the user. Thus, generation of a fixed amount of an aerosol with fixed quality is ensured.

BEST MODE OF CARRYING OUT THE INVENTION

Figure 1:
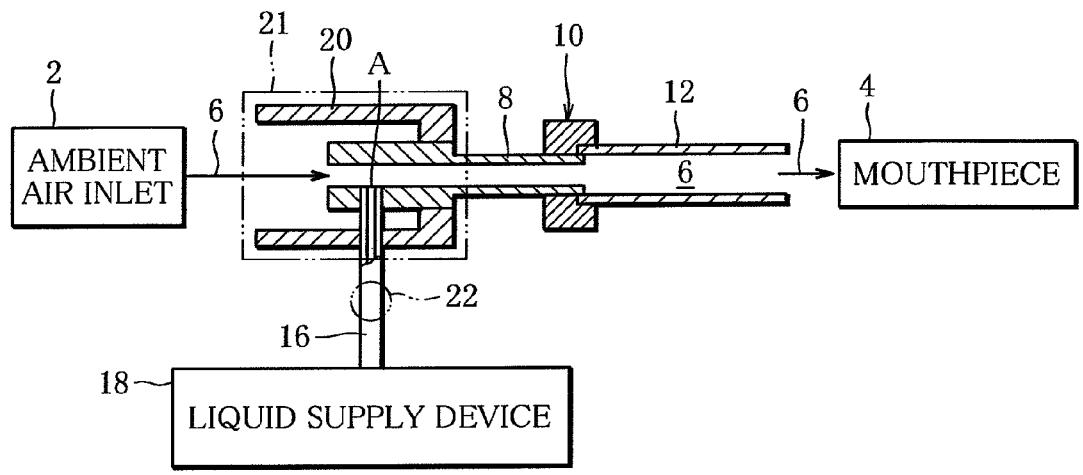
FIG. 1 is a schematic diagram showing a first embodiment of an aerosol inhalator.

Referring to FIG. 1, a first embodiment of the aerosol inhalator includes an outer casing (not shown). The outer casing has an ambient air inlet 2 at a front end thereof and a mouthpiece 4 at a rear end thereof. The mouthpiece 4 projects from the outer casing. The outer casing has an aerosol generation passage 6 defined therein. The aerosol generation passage 6 extends from the ambient air inlet 2 to the mouthpiece 4. Specifically, in the present embodiment, an air induction tube 8 and a tubular ceramic heater 12 constitute part of the aerosol generation passage 6.

The air induction tube 8 is made of stainless steel and has a stepped structure. Specifically, the air induction tube 8 has a large-diameter portion to the ambient air inlet 2 side, and a small-diameter portion to the mouthpiece 4 side. The small-diameter portion or the downstream end of the air induction tube 8 is connected to the ceramic heater 12 by an annular coupling 10. More specifically, the downstream end of the air induction tube 8 is inserted in the upstream end of the ceramic heater 12 so that a joint is formed by the downstream end and the upstream end. The coupling 10 surrounds the joint to hermetically connect the air induction tube 8 and the ceramic heater 12 together.

From the air induction tube 8, a tubular liquid passage 16 extends. Specifically, an end of the tubular liquid passage 16 is connected to the large-diameter or upstream portion of the air induction tube 8 at a feed position A. The other end of the tubular liquid passage 16 is connected to a portable liquid supply device 18. The liquid supply device 18 has a liquid chamber (not shown) therein, which contains a solution. From the liquid chamber, the solution can be fed toward the feed position A via the tubular liquid passage 16 in a fixed amount at a time. The liquid supply device 18 is therefore activated in advance of use of the inhalator, to fill the tubular liquid passage 16 with the solution up to the feed position A. Specifically, the liquid supply device 18 includes a syringe pump having the aforementioned liquid chamber as a pump chamber, and a drive source for driving the syringe pump.

Outside the air induction tube 8, a radiation cover 20 of aluminum is provided. The radiation cover 20 covers the upstream portion of the air induction tube 8 including the feed position A. Specifically, the radiation cover 20 is in the shape of a hollow cylinder, of which one end is closed by receiving the upstream portion of the air induction tube 8 and the other end is open toward the ambient air inlet 2. The radiation cover 20 has an inside diameter greater than the outside diameter of the upstream portion of the air induction tube 8, and has a coat (not shown) of black alumite over the entire surface thereof.

The inhalator also includes a power source switch (not shown) to switch the ceramic heater 12 on and off and a manually-operated liquid supply switch (not shown) to switch the liquid supply device 18 on and off.

When the user puts the power source switch in "on" position, the ceramic heater 12 is caused to warm up to its operating temperature and then maintained at the operating temperature. In this state, when the user puts the liquid supply switch in "on" position, the liquid supply device 18 is activated to feed a fixed amount of the solution further forward into the aerosol generation passage 6 from the feed position A through the tubular liquid passage 16. Simultaneously with putting the liquid supply switch in "on" position, the user sucks on the mouthpiece 4 to draw air along the aerosol generation passage 6, thus creates a drawn-in air flow, namely a flow of air from the ambient air inlet 2 toward the mouthpiece 4, in the aerosol generation passage 6. The drawn-in air flow carries the solution fed forward from the feed position A, toward the ceramic heater 12. The solution reaching the ceramic heater 12 in this manner immediately evaporates by being heated by the ceramic heater 12 and condenses in the drawn-in air flow, thus turns into an aerosol, which the user inhales with drawn-in air.

Although the solution fed from the feed position A into the aerosol generation passage 6 receives heat from the ceramic heater 12, an increase in temperature of the solution is restricted by the function of the radiation cover 20. Consequently, the solution fed into the aerosol generation passage 6 is prevented from immediately evaporating and escaping, near the feed position A, so that all the amount of the solution fed into the aerosol generation passage 6 turns into an aerosol after conveyed from the feed position A to the ceramic heater 12 by the user's sucking action, and is inhaled by the user.

If the radiation cover 20 were not provided, the solution fed from the feed position A would partly evaporate by receiving heat from the ceramic heater 12 and escape to the outside through the ambient air inlet 2. In this case, although the liquid supply device 18 feeds a fixed amount of the solution into the aerosol generation passage 6 simultaneously with the user's sucking action, the amount of the aerosol inhaled by the user fluctuates.

An experiment was conducted in which the ceramic heater 12 was warmed up to 300° C. and kept in that state for 10 minutes, during which the temperature at the feed position A was monitored. The experiment showed that the radiation cover 20 restricted the increase in temperature at the feed position A to approximately 60° C., while without the radiation cover 20, the temperature at the feed position A reached as high as approximately 160° C.

The size of the air induction tube 8, the ceramic heater 12 and the radiation cover 20 used in the experiment was as follows:

Air Induction Tube 8:
inside diameter=1.6 mm, outside diameter of the small-diameter portion=1.9 mm, length=15 mm, thickness=1 mm Ceramic Heater 12:
inside diameter=2.0 mm, outside diameter=4 mm, length=30 mm, resistance=0.4Ω

Radiation Cover 20:
Surface area=1160 mm$^2$, volume=412 mm$^3$

In place of or in addition to the aforementioned radiation cover 20, a heat pipe or a heat sink with a great heat capacity may be provided to the air induction tube 8. In this case, desirably, the heat pipe or heat sink should be connected to the air induction tube 8 near the feed position A. Alternatively, a Peltier element or a cooler using air, water or the like may be used to cool the air induction tube 8, as indicated in two-dot chain line in FIG. 1.

Figure 2:
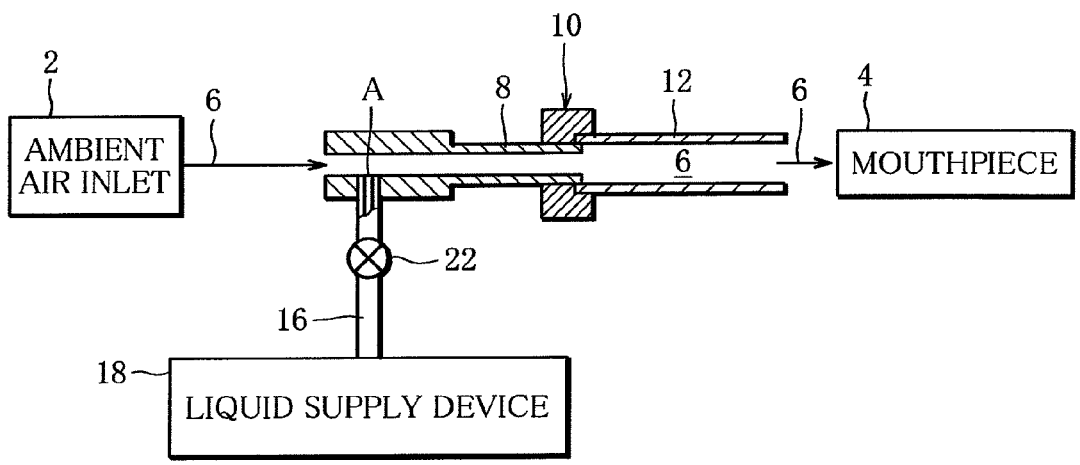
FIG. 2 is a schematic diagram showing a second embodiment of the aerosol inhalator.

FIG. 2 shows a second embodiment of the aerosol inhalator.

In the description of the second embodiment of the inhalator, components identical in function to those of the first embodiment of the inhalator will be assigned the same reference characters, while the description of such components will be omitted.

The second embodiment of the inhalator includes an open-close valve 22. The open-close valve 22 is provided to the tubular liquid passage 16. The inhalator also includes a pressure-type suction sensor (not shown) detecting the user's sucking action. When the suction sensor detects the user's sucking action, the open-close valve 22 is opened. Except while the suction sensor is detecting the user's sucking action, the open-close valve 22 is held closed.

Also the liquid supply device 18 is activated according to a detection signal from the suction sensor. Specifically, the liquid supply device 18 feeds a fixed amount of the solution from the feed position A into the aerosol generation passage 6 in conjunction with the user's sucking action, thus according to the detection signal from the suction sensor. The solution fed in this manner is immediately conveyed from the feed position A to the ceramic heater 12 and turns into an aerosol.

As seen from the above, except while the user is doing a sucking action, the open-close valve 22 is held closed. The pump chamber of the liquid supply device 18 is therefore hermetically sealed, so that the solution in the pump chamber is prevented from being exposed to ambient air entering through the ambient air inlet 2 and the mouthpiece 4. Consequently, even if the solution in the pump chamber contains volatile constituents, such as aromatic substances, and heat transferred from the ceramic heater 12 to the solution in the pump chamber causes the volatile constituents to evaporate and escape from the solution, the evaporated volatile constituents are not allowed to escape into the ambient air. The solution in the pump chamber is therefore effectively protected against alteration.

In FIG. 1, an open-close valve 22 is indicated in two-dot chain line to show that the open-close valve 22 can be used with the radiation cover 20 and/or the cooling device 21.

A variety of commercially-available valves can be used for the open-close valve 22. If the tubular liquid passage 16 is made of a rubber tube capable of elastic deformation, for example, the open-close valve may be one that includes part of the rubber tube as a valve passage. Such open-close valve closes the valve passage by elastically deforming and squeezing the rubber tube and opens the valve passage by ceasing to squeeze the rubber tube, thus allowing the rubber tube to return to its original shape by virtue of its elasticity.

Figure 3:
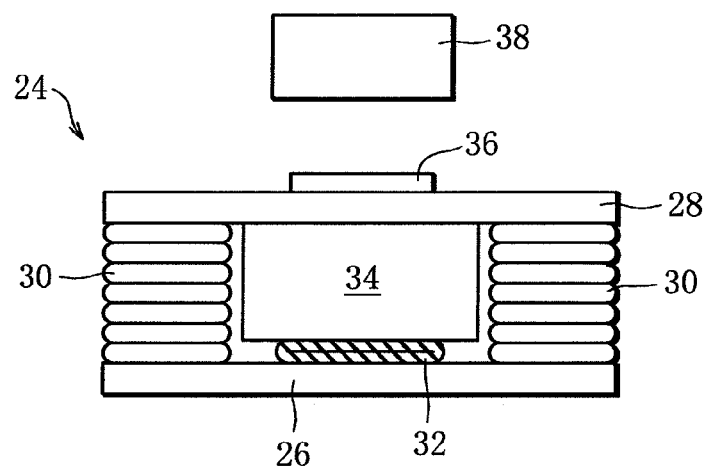
FIG. 3 is a diagram specifically showing an open-close valve indicated in FIG. 2 in closed position.
Figure 4:
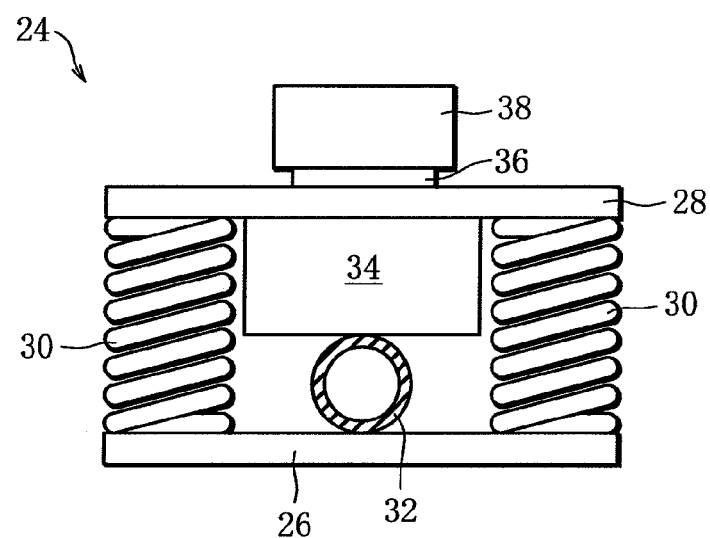
FIG. 4 is a diagram showing the open-close valve of FIG. 3 in open position.

An example of such open-close valve is shown in FIGS. 3 and 4.

The open-close valve 24 shown in FIG. 3 includes a fixed plate 26 and a movable plate 28 arranged apart from the fixed plate 26. The fixed plate 26 may be a wall of the aforementioned outer casing. A pair of valve springs 30 is arranged between the fixed plate 26 and the movable plate 28. The valve springs 30 are tension springs. Each valve spring 30 is connected to the fixed plate 26 and the movable plate 28 to pull the movable plate 28 toward the fixed plate 26.

The rubber tube 32 as the tubular liquid passage 16 has resistance to high temperatures and extends through between the two valve springs 30. In the present embodiment, the rubber tube 32 is fixed to the fixed plate 26. As seen in FIG. 3, a pusher 34 is mounted on the lower surface of the movable plate 28. When the movable plate 28 is held in the position shown, the rubber tube 32 is elastically deformed and squeezed by the pusher 34. Thus, the rubber tube 32, namely the valve passage of the open-close valve 24 is closed.

A magnet 36 is mounted on the upper surface of the movable plate 28, while a solenoid 38 is arranged above the movable plate 28. In the state shown in FIG. 3, when the solenoid 38 is excited, the solenoid 38 attracts the magnet 36 upward. Consequently, the magnet 36 moves up with the movable plate 28 and the pusher 34, against the urging force of the valve springs 30, so that the pusher 34 draws back from the rubber tube 32 and ceases to squeeze the rubber tube 32, as shown in FIG. 4. The rubber tube 32 therefore returns to the original shape by virtue of its elasticity, and thus, the valve passage, therefore the open-close valve 24 is opened.

It may be arranged such that the open-close valve 24 is opened in conjunction with the user's suction action or the user's putting the power source switch in "on" position.

Figure 5:
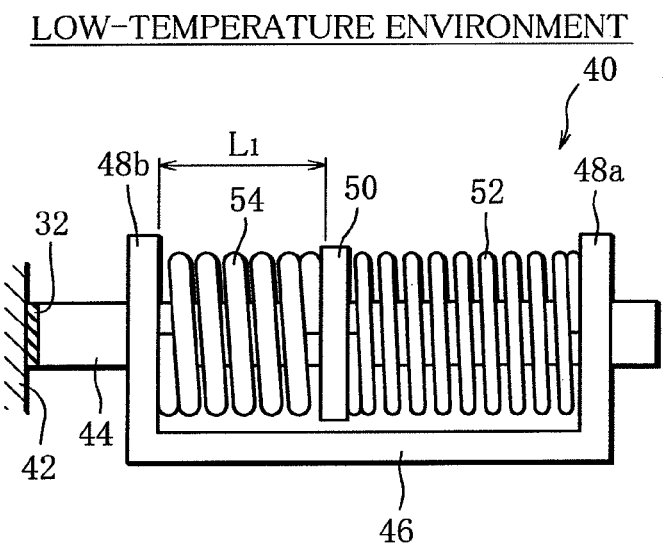
FIG. 5 is a diagram showing a variant of the open-close valve in closed position.
Figure 6:
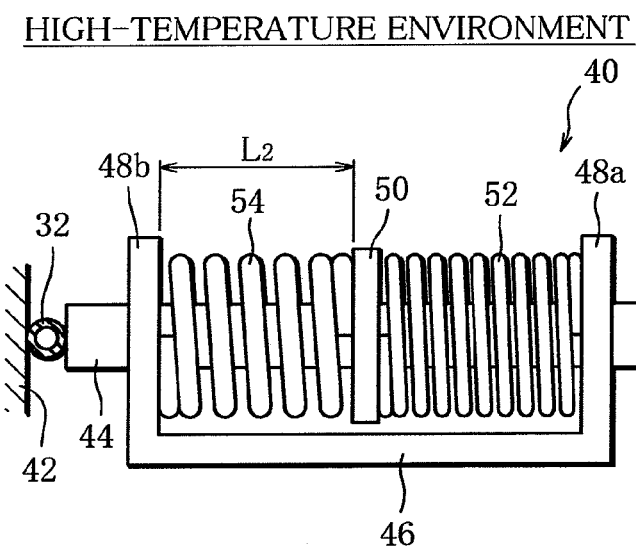
FIG. 6 is a diagram showing the open-close valve of FIG. 5 in open position.

FIGS. 5 and 6 show a variant of the open-close valve.

The open-close valve 40 includes a fixed wall 42. A rubber tube 32 is fixed to the fixed wall 42. Like the aforementioned fixed plate 26, the fixed wall 42 may be a wall of the outer casing.

A push rod 44 is arranged near the rubber tube 32. The push rod 44 extends at right angles to the fixed wall 42 and is supported by a rod holder 46. More specifically, the rod holder 46 includes a pair of support walls 48a, 48b. The support walls 48 are apart from each other in the direction of axis of the push rod 44. The push rod 4 is slidably passed through the support walls 48a, 48b, and thus, supported by the support walls 48a, 48b.

The push rod 44 has a flange 50 on the outer circumferential surface thereof. The flange 50 is located between the paired support walls 48a, 48b. Between the support wall 48a and the flange 50, a valve spring 52, which is a stainless compression spring, is disposed so as to surround the push rod 44. The valve spring 52 functions similarly to the aforementioned valve spring 30.

The valve spring 52 urges or pushes the flange 50, that is, the push rod 44 toward the rubber tube 32. The push rod 44 is thus held in a position to elastically deform and squeeze the rubber tube 32, as shown in FIG. 5, so that the open-close valve 40 is held closed.

Between the support wall 48b and the flange 50, on the other hand, a control spring 54, which is a compression spring, is disposed. The control spring 54 is made of a shape-memory alloy. The spring constant of the control spring 54 varies depending on the temperature of the surroundings or itself. More specifically, in a low-temperature environment in which the surroundings or the control valve itself is at low temperatures, the control spring 54 has a spring constant smaller than that of the valve spring 52. In a high-temperature environment in which the surroundings or the control valve itself is at temperatures higher than a certain temperature, the control spring 54 has a spring constant greater than that of the valve spring 52.

The temperature of the control spring 54 itself can be varied by controlling supply of electricity to the control spring 54.

In the open-close valve 40 in the low-temperature environment, the valve spring 52 holds the push rod 44 pressed against the rubber tube 32, against the urging force of the control spring 52. Consequently, the open-close valve 40 is held closed. The length between the flange 50 and the support wall 48b when the open-close valve is closed is denoted by L1.

In the open-close valve 40 in the high-temperature environment, on the other hand, the urging force of the control spring 54 overcomes that of the valve spring 52. The push rod 44 is therefore drawn back from the rubber tube 32 and thus ceases to squeeze the rubber tube 32, as shown in FIG. 6, so that the open-close valve 40 is opened. The length between the support wall 48b and the flange 50 when the open-close valve is open is denoted by L2 (>L1).

As described above, the open-close valve 40 is opened and closed depending on the ambient temperature. Consequently, while the ceramic heater 12 is maintained at its operating temperature so that the open-close valve 40 is in a high-temperature environment created by heat from the ceramic heater 12, the open-close valve 40 is held open. While the ceramic heater 12 is not operating so that the open-close valve 40 is in a low-temperature environment, the open-close valve 40 is held closed. In this case, the open-close valve 40 is opened or closed in conjunction with the aforementioned power source switch being put in "on" or "off" position.

The open-close valve 40 can be opened or closed also by controlling supply of electricity to the control spring 54, independently of the power source switch being put in "on" or "off" position. It can therefore be arranged such that the open-close valve is held open only during the user's sucking action.

The invention claimed is:

1. An aerosol inhalator comprising:
    an aerosol generation passage extending from an ambient air inlet to a mouthpiece;
    a liquid supply device including a liquid chamber storing a solution from which an aerosol is to be generated, for being capable of feeding a predetermined amount of the solution to a feed position defined in said aerosol generation passage;
    a heating device disposed on said aerosol generation passage, downstream of the feed position, for heating the solution conveyed from the feed position toward the mouthpiece with a drawn-in flow of air created in said aerosol generation passage by the mouthpiece being sucked on, thereby causing the solution to evaporate and turn into an aerosol; and
    a protector provided on a pathway from said heating device to said liquid supply device via the feed position, to protect the solution at the feed position and in the liquid chamber from environment.

2. The aerosol inhalator according to claim 1, wherein said protector includes a reduction device arranged near the feed position to reduce heat transfer from said heating device to the feed position.

3. The aerosol inhalator according to claim 2, wherein the reduction device includes a radiation member surrounding said aerosol generation passage.

4. The aerosol inhalator according to claim 1, wherein said protector includes a cooling device arranged near the feed position.

5. The aerosol inhalator according to claim 1, wherein said protector includes a valve arranged between the feed position and said liquid supply device.

6. The aerosol inhalator according to claim 5, wherein the valve is held open only while air in said aerosol generation passage is being sucked through the mouthpiece.

7. The aerosol inhalator according to claim 5, wherein the valve includes
    an elastically-deformable tube connecting the feed position and said liquid supply device, the elastically-deformable tube having a part as a valve passage, and
    a movable member disposed near the tube to be movable between a "close" position in which the movable member elastically deforms and squeezes the tube to close the valve passage and an "open" position in which the movable member is drawn back from the tube to open the valve passage.

8. The aerosol inhalator according to claim 7, wherein the valve further includes
    a fixed member capable of pinching the tube in cooperation with the movable member,
    a valve spring holding the movable member in the "close" position, and
    an actuator for moving the movable member to the "open" position against urging force of the valve spring.

9. The aerosol inhalator according to claim 8, wherein the actuator includes a magnet mounted on the movable member and a solenoid capable of attracting the magnet.

10. The aerosol inhalator according to claim 8, wherein the actuator includes a control spring made of a shape-memory alloy.

* * * * *